(12) United States Patent
Berger et al.

(10) Patent No.: US 8,835,514 B2
(45) Date of Patent: Sep. 16, 2014

(54) PSEUDO-THERMOSETTING NEUTRALIZED CHITOSAN COMPOSITION FORMING A HYDROGEL AND A PROCESS FOR PRODUCING THE SAME

(75) Inventors: Jérôme Berger, Bière (CH); Robert Gurny, Genéve (CH); Marianne Reist Oechslin, Ecublens (CH)

(73) Assignee: Laboratoire Medidom S.A., Geneva (CH)

( * ) Notice: Subject to any disclaimer, the term of this patent is extended or adjusted under 35 U.S.C. 154(b) by 1698 days.

(21) Appl. No.: 10/593,678

(22) PCT Filed: Mar. 22, 2004

(86) PCT No.: PCT/EP2004/002988
§ 371 (c)(1),
(2), (4) Date: Sep. 21, 2006

(87) PCT Pub. No.: WO2005/097871
PCT Pub. Date: Oct. 20, 2005

(65) Prior Publication Data
US 2007/0141142 A1 Jun. 21, 2007

(51) Int. Cl.
*A61K 47/00* (2006.01)
*C08J 3/075* (2006.01)
*A61K 47/36* (2006.01)
*A61K 9/06* (2006.01)

(52) U.S. Cl.
CPC .............. *C08J 3/075* (2013.01); *A61K 47/36* (2013.01); *A61K 9/06* (2013.01); *C08J 2305/08* (2013.01)
USPC ........................................ 514/777

(58) Field of Classification Search
USPC ........................................ 514/777
See application file for complete search history.

(56) References Cited

U.S. PATENT DOCUMENTS

| 4,659,700 A | 4/1987 | Jackson .......................... 514/55 |
| 4,996,307 A | 2/1991 | Itoi et al. ....................... 536/20 |
| 6,344,488 B1 | 2/2002 | Chenite et al. |
| 2004/0171151 A1* | 9/2004 | Domard et al. ................ 435/395 |
| 2010/0113618 A1 | 5/2010 | Berger et al. .................. 514/777 |

FOREIGN PATENT DOCUMENTS

| JP | 62-004702 | 10/1987 | ............. C08B 37/08 |
| JP | 2001-513367 | 4/2001 | ............. A61L 27/00 |
| JP | 2007-090005 | 4/2007 | ............. A63B 23/02 |
| JP | 2010-072502 | 4/2010 | ............ G02F 1/1333 |
| WO | WO 99/07416 | 2/1999 | ............. A61L 25/00 |
| WO | WO 02/078760 | * 10/2002 | ............. A61L 27/38 |
| WO | WO-02/078760 A | 10/2002 | |
| WO | WO 03/011912 | * 2/2003 | ............. C08B 37/00 |
| WO | WO-03/068281 A | 8/2003 | |

OTHER PUBLICATIONS

Industrial Research Ltd Catalog (accessed online at http://www.irl.cri.nz/productsandservices/products-fine-chemicals/Squidpenderivedchitinandchitosan.aspx on Jan. 14, 2009).*
Granja et al (Key Engineering Materials vols. 254-256, 2004).*
Baumann et al (Carbohydrate Res 1:43-57, 2001).*
Nettles et al (Tissue Engineering 8:1009-1016, 2002).*
Pierre Sorlier et al.: "Relation between the degree of acetylation and the electrostatic properties of chitin and chitosan," Biomacromolecules, vol. 2, 2001, pp. 765-772, XP002306956 (English abstract attached).
Office Action Dated Nov. 16, 2012 issued in U.S. Appl. No. 12/654,700.
Shigehiro Hirano et al.: "N-acetylation of chitosan and the rate of its enzymic hydrolysis," Biomaterials, vol. 10, Oct. 1, 1989, pp. 574-576, XP002306957.
International Search Report for PCT/EP2004/002988 (WO 2005/097871), dated Nov. 23, 2004; ISA/EP.

* cited by examiner

*Primary Examiner* — Paul Zarek
(74) *Attorney, Agent, or Firm* — Harness, Dickey & Pierce, P.L.C.

(57) ABSTRACT

The composition disclosed is a pseudo-thermosetting neutralized chitosan composition, neutralized with an hydroxylated base, forming a phosphate-free transparent hydrogel at a temperature higher than 5° C. Said composition contains a homogeneously reacetylated chitosan derived from a chitosan having a deacetylation degree of 80-90%, having a molecular weight of not smaller than 200 kDa and a deacetylation degree of 30-60%, and may further contain a diol. Said composition may be used as a drug delivery system.

4 Claims, 1 Drawing Sheet

Elastic modulus (G') of three hydrogels as a function of time when temperature increases from 4 to 37°C.
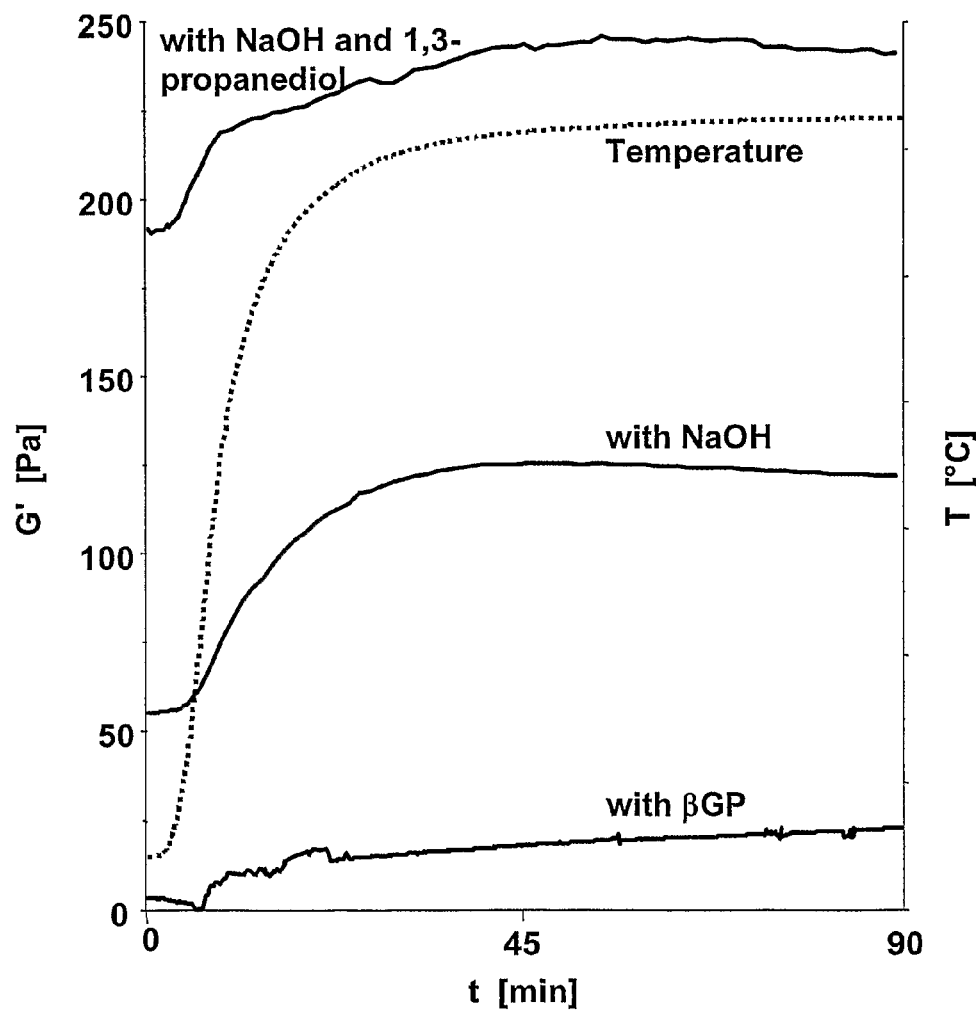
"With NaOH" refers to the hydrogel obtained in Example 6
"With NaOH and 1,3-propanediol": refers to hydrogel obtained in Example 7
"With β-GP": refers to comparative hydrogel obtained in Example 10 (Comparative)

PSEUDO-THERMOSETTING NEUTRALIZED CHITOSAN COMPOSITION FORMING A HYDROGEL AND A PROCESS FOR PRODUCING THE SAME

FIELD OF THE INVENTION

The present invention relates to a pseudo-thermosetting neutralized chitosan composition forming a phosphate-free, transparent hydrogel at a temperature higher than 5° C., and to a process for producing the same.

Still further, the present invention relates to a process for producing a homogeneously reacetylated chitosan, to a homogeneously reacetylated chitosan obtained by said process for use in the preparation of a pseudo-thermosetting neutralized chitosan composition forming a phosphate-free, transparent hydrogel at a temperature higher than 5° C., and to the use of a pseudo-thermosetting neutralized chitosan composition as a drug delivery system.

BACKGROUND OF THE INVENTION

Hydrogels, which may be defined as macromolecular networks swollen in water or biological fluids, are known for various biomedical applications.

Further, hydrogels exhibiting the specific property of having their viscosity increasing when the temperature increased, also called "thermosensitive hydrogels", were proved to have a facilitated application combined with an increased residence time at the site of application and therefore were found advantageous as drug delivery system.

As known from O. Felt et al. in The Encyclopedia of Controlled Drug Delivery, 1999, said thermosensitive hydrogels may be based advantageously on polymers of natural origin, for example on chitosan which is a commercially available inexpensive polymer derived from chitin, the second most abundant polysaccharide after cellulose.

Chitosan is known as a chitin derivative obtained by partial to substantial alkaline N-deacetylation of chitin also named poly(N-acetyl-D-glucosamine), which is a naturally occurring biopolymer, found in hard shells of marine living animals such as fishes, crustaceous, shrimps, crabs, etc., or synthesized by natural organisms such as zygomycete, fungi, etc.

Chitosan contains free amine (—$NH_2$) groups and may be characterized as to the proportion of N-acetyl-D-glucosamine units and D-glucosamine units, and such is expressed as the degree of deacetylation (DD) of the fully acetylated polymer chitin.

Parameters of chitosan influencing important properties such as solubility and viscosity are the degree of deacetylation (DD) which may be understood as representing the percentage of deacetylated monomers, and the molecular weight (MW).

Chitosan is known to be biodegradable, biocompatible, bioadhesive, bacteriostatic, and further to promote wound-healing, drug absorption, and tissue reconstruction.

Due to its above mentioned intrinsic properties, chitosan is known to have numerous cosmetic and pharmaceutical activities, and has been also widely explored for various applications through gels.

Therefore, considering the advantageous properties of chitosan, there is a continuous need to improve the properties of known thermosensitive chitosan hydrogels which are still considered as very promising for a wider range of biomedical applications.

WO-A-99/07416 (Biosynthec) discloses a pH-dependent temperature-controlled chitosan hydrogel which has thermosensitive properties at neutral pH such that it has low viscosity in the cold but gels at body temperature.

This thermosensitive chitosan hydrogel is prepared by neutralizing a commercial chitosan having a deacetylation degree of about 80% with mono-phosphate dibasic salts of polyols or sugars exemplified in particular by β-glycerophosphate (β-GP).

Addition of β-GP to chitosan allows to increase the pH up to 7 without chitosan precipitation and to form a hydrogel on a temperature dependant way, i.e. the higher is the temperature, the faster is the gelation process.

Said hydrogels are advantageous in that they contain biocompatible components and a high percentage of water, in that they have a physiological pH and in that no heat nor product is released during gelation.

As also reported by A. Chenite et al. in Carbohydr. Polym. 46, 39-47 (2001), in relation with chitosan/β-GP pseudo-thermosetting hydrogels, adding β-GP for neutralizing high DD chitosan which are known to precipitate above pH 6.2 allows to prevent precipitation of said high DD chitosan.

However, presence of β-GP in the hydrogel leads to the following disadvantages.

β-GP is a negatively charged entity that can react with a positively charged bioactive component, leading to its precipitation or to the disturbance of its liberation from the hydrogel.

Therefore, presence of β-GP renders chitosan/β-GP hydrogels inappropriate for use with numerous drugs.

Further, the modulation of the properties of this hydrogel, such as gelation time and viscosity, depends on the concentration of β-GP and is therefore limited by the solubility of β-GP.

In particular, a high concentration of β-GP is required to have a low gelation time avoiding the rapid elimination of the hydrogel after its administration.

However, a high concentration of β-GP also decreases the viscosity of the hydrogel.

Therefore, the gelation time has to be balanced with the consistency of the hydrogel, and it is not possible to obtain gels that have both a low gelation time and a high viscosity, which would be a desirable combination of characteristics.

Also, a too high concentration of β-GP may induce the precipitation of the hydrogel at its administration site.

Further, said thermosensitive chitosan/β-GP hydrogels were found to be turbid, thus rendering their use inappropriate for particular applications such as ocular or topic administrations.

On the basis of these facts, the present inventors have continued their researches to overcome the disadvantages of the known thermosensitive chitosan/β-GP hydrogels and have surprisingly found that by using a reacetylated chitosan having a deacetylation degree of 30-60%, neutralization of chitosan to form thermosensitive hydrogel may be made by addition of NaOH or any other hydroxylated base instead of β-glycero-phosphate, and further that if reacetylation of chitosan to DD 30-60% is made in homogeneous conditions, a transparent chitosan hydrogel is obtained.

The present invention has been achieved on the basis of these results.

SUMMARY OF THE INVENTION

According to a first aspect, the present invention provides a pseudo-thermosetting neutralized chitosan composition, which comprises 0.1 to 2.0 wt/v %, preferably 0.5 to 1 wt/v %, based on the total composition, of a homogeneously reacetylated chitosan derived from a chitosan having a deacetylation degree of 80-90%, having a molecular weight of not smaller than 200 kDa, preferably not smaller than 600 kDa, and a deacetylation degree of 30-60%, preferably 45 to 55%, neutralized with an hydroxylated base, wherein said composition forms a phosphate-free transparent hydrogel at a temperature higher than 5° C. In a preferred embodiment, the pseudo-thermosetting neutralized chitosan composition further comprises a diol having a distance of at least 4.7 Å between its hydroxyl groups, preferably 1,3-propanediol.

According to a second aspect, the present invention provides a process for producing a homogeneously reacetylated chitosan having a molecular weight of not smaller than 200 kDa and a deacetylation degree of 30-60% which comprises the steps of: a) filtrating a chitosan having a molecular weight of not smaller than 200 kDa and a deacetylation degree of 80 to 90% dissolved in an acidic medium to eliminate insoluble particles; b) precipitating chitosan contained in the filtrated acidic solution obtained in step a) to obtain chitosan free of insoluble particles; c) preparing a cooled acidic solution of the chitosan free of insoluble particles obtained in step b) at a temperature lower than 5° C. to obtain a cooled acidic solution of chitosan free of insoluble particles; d) preparing a cooled acetic anhydride solution containing a predetermined amount of acetic anhydride in methanol at a temperature lower than 5° C.; e) reacetylating chitosan by adding, under homogeneous conditions, the cooled acetic anhydride solution of step d) to the cooled solution of chitosan prepared in step c) to provide a crude homogeneously reacetylated chitosan having a deacetylation degree of 30-60% ; f) treating said crude chitosan obtained in step e) to eliminate salts produced during reacetylation and insoluble particles of chitosan to obtain a homogeneously reacetylated chitosan having a deacetylation degree of 30-60%. In a preferred embodiment, the treating step f) includes the steps of: f-1) dialyzing chitosan obtained in step e) to eliminate salts produced during reacetylation in order to obtain a homogeneously reacetylated chitosan solution; f-2) filtrating the chitosan solution obtained in step f-1) to eliminate insoluble particles of chitosan; f-3) precipitating chitosan contained in the filtrated solution obtained in step f-2) and then drying chitosan to obtain a homogeneously reacetylated chitosan having a deacetylation degree of 30-60%. Preferably, the precipitating step f-3) includes addition of a mixture of $NH_4OH$/methanol.

According to a third aspect, the present invention provides a homogeneously reacetylated chitosan having a molecular weight of not smaller than 200 kDa and a deacetylation degree of 30-60% obtained by the process according to the second aspect of the present invention, for use in the preparation of a pseudo-thermosetting neutralized chitosan composition forming a phosphate-free transparent hydrogel at a temperature higher than 5° C.

According to a fourth aspect, the present invention provides a process for producing a pseudo-thermosetting neutralized chitosan composition forming a phosphate-free, transparent hydrogel at a temperature higher than 5° C., which comprises the steps of: g) solubilizing a homogeneously reacetylated chitosan derived from a chitosan having a deacetylation degree of 80-90%, having a molecular weight of not smaller than 200 kDa and a deacetylation degree of 30-60%, in an aqueous HCl medium and cooling said acidic chitosan solution at a temperature lower than 5° C.; h) neutralizing the cooled chitosan solution obtained in step g) by adding an aqueous hydroxylated base, preferably NaOH, previously cooled at a temperature lower than 5° C. to the cooled chitosan solution until the cooled solution of chitosan exhibits a pH of 6.8 to 7.2, preferably a pH of 7; i) optionally, increasing the temperature of the neutral cooled solution of chitosan obtained in step h) at a temperature higher than 5° C. in order to induce pseudo-thermogelation. In a preferred embodiment, the process further comprises a step of sterilizing chitosan before the step g) of solubilization. In a still preferred embodiment, the process further comprises the step of adding an appropriate amount of a diol having a distance of at least 4.7 Å between the hydroxyl groups, preferably 1,3-propanediol, before, during or after solubilization step g), or before, during or after the neutralization step h) to increase the consistency of the hydrogel to the required degree of consistency of the hydrogel. In a still further preferred embodiment, the homogeneously reacetylated chitosan solubilized in step g) is obtained by the process according to the second aspect of the present invention.

According to a fifth aspect, the present invention provides a phosphate-free transparent pseudo-thermosetting chitosan hydrogel obtained by the process according to the fourth aspect of the present invention.

According to a sixth aspect, the present invention provides a use of a homogeneously reacetylated chitosan having a deacetylation degree of 30-60% and a molecular weight of not smaller than 200 kDa obtained by the process according to the second aspect of the present invention, for the preparation of a phosphate-free, transparent, pseudo-thermosetting chitosan hydrogel.

According to a seventh aspect, the present invention provides a use of a pseudo-thermosetting neutralized chitosan composition according to the first aspect of the present invention, as a drug delivery system.

According to the present invention, using a reacetylated chitosan having a deacetylation degree of 30-60% allows advantageously to use NaOH or any other hydroxylated base to neutralize the chitosan instead of using β-glycero-phosphate and therefore allows to obtain a phosphate-free chitosan hydrogel.

Further, according to the present invention, using a reacetylated chitosan which has been reacetylated in homogeneous conditions to a deacetylation degree of 30-60% allows advantageously to obtain a transparent chitosan hydrogel.

Still further, according to the present invention, addition of diols having a minimal distance of 4.7 Å between the hydroxyl groups allows advantageously to modulate the viscoelastic properties of the hydrogel.

Other advantages of the present invention will appear in the following description.

The present invention will be now described in a more detailed manner.

BRIEF DESCRIPTION OF THE FIGURE

The FIGURE shows the elastic modulus (G') of two phosphate-free, transparent chitosan hydrogels of the present invention obtained in Examples 6 and 7, and of a comparative phosphate-containing chitosan hydrogel obtained in Example 10 (Comparative) as a function of time when temperature increases from 4 to 37° C.

DETAILED DESCRIPTION OF THE INVENTION

It is to be noted that in the present description and claims, the expression "pseudo-thermosetting" in connection with the composition of the present invention means that temperature does not induce the gelation of the composition but acts rather as a catalyst which dramatically shortens the gelation time when risen.

It is also to be noted that in the present description and claims, the term "neutralized" means a pH of 6.8-7.2.

According to the present invention, the pseudo-thermosetting neutralized chitosan composition forming a phosphate-free transparent hydrogel at a temperature higher than 5° C. comprises a homogeneously reacetylated chitosan neutralized with an hydroxylated base.

The average molecular weight (MW) of the homogeneously reacetylated chitosan used in the present invention must be not smaller than 200 kDa.

Molecular weight of chitosan may be easily determined by size exclusion chromatography as reported for example by O. Felt, P. Furrer, J. M. Mayer, B. Plazonnet, P. Burri and R. Gurny in *Int. J. Pharm.* 180, 185-193 (1999).

Chitosan of molecular weights lower than 200 kDa is not appropriate for use in the present invention because it would not allow the formation of a pseudo-thermosetting composition forming a firm hydrogel.

Preferably, the homogeneously reacetylated chitosan used in the present invention has a molecular weight of not lower than 600 kDa.

The upper limit of MW is determined by the ease of administration, which depends on the chosen application.

Homogeneously reacetylated chitosan used in the present invention must have a deacetylation degree of 30-60% which means that the chitosan comprises 30 to 60% of D-glucosamine units and 70 to 40% of neutral N-acetyl-D-glycosamine units, respectively.

The deacetylation degree of chitosan may be determined by a spectrophotometric method such as described in the literature by R. A. Muzarelli and R. Richefti in Carbohydr. Polym. 5, 461-472, 1985 or R. A. Muzarelli and R. Richetti in "Chitin in Nature and Technology", Plenum Press 385-388, 1986. Briefly, in the latter method for example, chitosan is solubilized in 1% acetic acid and the DD is determined by measuring its content of N-acetyl-glucosamine by UV at $\lambda$ 200, 201, 202, 203 and 204 nm using N-acetyl-D-glucosamine solutions as standards.

If deacetylation degree of chitosan is lower than 30%, the chitosan becomes a polymer close to chitin that is insoluble in acidic conditions and consequently not usable in the present invention.

If deacetylation degree of chitosan is higher than 60%, the chitosan does not allow the preparation of a composition forming a phosphate-free transparent hydrogel.

In the present invention, in addition to the proportion of acetylated and deacetylated monomers of chitosan represented by its degree of deacetylation, the homogeneous distribution mode of these monomers is an essential criteria to get transparent and phosphate-free hydrogels.

In order to obtain such homogeneous distribution mode of acetylated and deacetylated monomers, the chitosan used for preparing the pseudo-thermosetting composition forming a hydrogel must be a chitosan derived from a chitosan having a deacetylation degree of 80-90% which has been homogeneously reacetylated to a deacetylation degree of 30-60% in conditions allowing a random distribution of acetylated and deacetylated monomers.

If the chitosan is reacetylated in a non-homogeneous manner, the chitosan does not allow the preparation of a transparent hydrogel.

Preferably, the homogeneously reacetylated chitosan used in the present invention has a deacetylation degree of 45 to 55%.

An homogeneously reacetylated chitosan having a molecular weight of not smaller than 200 kDa and a deacetylation degree of 30-60% for use in the preparation of a pseudo-thermosetting neutralized chitosan composition forming a phosphate-free, transparent hydrogel of the present invention may be prepared from a commercially available chitosan having a molecular weight of not smaller than 200 kDa and a deacetylation degree of 80 to 90% according to a new process forming part of the present invention which is based on the reacetylation method of chitosan with acetic anhydride described by Hirano (Hirano S. et al., *Carbohydr. Res.* 47, 315-320 (1976).

In step a) of the process of the present invention for preparing a homogeneously reacetylated chitosan, a commercial chitosan having a molecular weight not smaller than 200 kDa and a deacetylation degree of 80 to 90%, dissolved in an acidic medium, is filtrated to eliminate insoluble particles.

An example of commercial chitosan which may be used in the process of the present invention is a chitosan of pharmaceutical grade and high MW obtained from Aldrich Chemical, Milwaukee, USA, having a MW of 1'100 kDa as determined by size exclusion chromatographic method reported by O. Felt, et al. in *Int. J. Pharm.* 180, 185-193 (1999) and a deacetylation degree DD of 83.2% as measured by UV method reported by R. A. Muzarelli et al. in "Chitin in Nature and Technology", Plenum Press, New York, 385-388, (1986).

However, any commercial chitosan having a deacetylation degree of 80 to 90% and a molecular weight not smaller than 200 kDa may be used.

The acidic medium used for dissolving commercial chitosan may be for example 10% acetic acid and the acidic solution of chitosan obtained after solubilization of chitosan may be then diluted with an alcohol, for example methanol.

The acidic solution containing chitosan must be filtered to eliminate insoluble particles because presence of insoluble particles does not allow a subsequent homogeneous reacetylation.

Said filtration may be made for example in two times, first through a 100 μm filter and then through a 5 μm filter, but any other mesh sizes may be used.

Then, in step b) of the process of the present invention for preparing a homogeneously reacetylated chitosan, chitosan contained in the filtrated acidic solution is precipitated, for example by adding a 0.2 M $NH_4OH$/methanol (50/50) solution.

After precipitation, the chitosan may be further washed, for example with methanol, and then dried according to conventional methods, for example in the presence of Silicagel, under vacuum, at room temperature and protected from light.

In step c) of the process of the present invention for preparing a homogeneously reacetylated chitosan, chitosan obtained in step b) is further dissolved in an acidic medium, for example 10% acetic acid, and the acidic solution of chitosan obtained may be diluted, for example with methanol. Said acidic solution is then cooled at a temperature lower than 5° C., thus obtaining a cooled acidic solution of chitosan free of insoluble particles.

According to step d) of the process of the present invention for preparing a homogeneously reacetylated chitosan, it is prepared separately an acetic anhydride solution containing a predetermined amount of cooled acetic anhydride in cooled methanol (for example in an ice-bath), so this solution is at a temperature lower than 5° C.

According to step e) of the process of the present invention for preparing a homogeneously reacetylated chitosan, chitosan is reacetylated by adding dropwise, under homogeneous conditions, the cooled acetic anhydride solution containing a predetermined amount of acetic anhydride to the cooled acidic solution containing chitosan in order to provide a chitosan having a deacetylation degree of 30-60%.

A temperature of the acetic anhydride solution and/or of the cooled chitosan solution higher than 5° C. would not allow a homogeneous reacetylation.

The amount of acetic anhydride contained in the acetic anhydride solution will depend on the amount of the chitosan to reacetylate, on the degree of deacetylation of the commercial starting chitosan and on the degree of deacetylation that is intended to obtain.

Therefore, said amount of acetic anhydride contained in the acetic anhydride solution will be determined from case to case.

Preferably, said amount of acetic anhydride will be predetermined to obtain a degree of deacetylation of the reacetylated chitosan of 45 to 55%.

Homogeneous conditions during the addition step e) is an essential feature of this process, and they may be obtained by providing a fast stirring during the addition, for example with a stirring propeller.

An inadequate stirring, for example with a magnetic stirrer, does not allow a homogeneous reacetylation of chitosan and therefore, the chitosan obtained would not allow the preparation of a pseudo-thermosetting composition forming a transparent hydrogel.

After addition of cooled acetic anhydride solution to the cooled solution containing chitosan, the solution containing homogeneously reacetylated chitosan may be kept further under stirring at a temperature lower than 5° C. to ensure complete reaction and then may be kept at room temperature where it turns into a gel.

According to step f) of the process of the present invention for preparing a homogeneously reacetylated chitosan, the crude homogeneously reacetylated chitosan obtained after the reacetylation step e) must be treated to eliminate salts produced during reacetylation and to further eliminate insoluble particles.

Said treatment may be preferably carried out by dialyzing homogeneously reacetylated chitosan, for example in the gel form which may be obtained after step e), against deionized water for a sufficient time to eliminate the salts produced during reacetylation, thus leading to a chitosan viscous solution, then by filtering the chitosan viscous solution through a 100 μm filter or other size filter in order to eliminate insoluble particles of chitosan.

Homogeneously reacetylated chitosan having a deacetylation degree of 30-60% for use in the preparation of a phosphate-free, transparent chitosan hydrogel may be recovered for example after precipitation by addition of 0.2 M $NH_4OH$/methanol (50/50), washing, for example, with methanol, and drying, for example in the presence of Silicagel, under vacuum, at room temperature and protected from light.

The pseudo-thermosetting neutralized chitosan composition forming a phosphate-free, transparent hydrogel of the present invention is prepared according to a new process forming part of the present invention, using a homogeneously reacetylated chitosan prepared according to steps a) to f) of the process for preparing a homogeneously reacetylated chitosan forming part of the present invention.

If the chitosan is not homogeneously reacetylated, the obtained hydrogel will be turbid or chitosan could precipitate during neutralization.

Typically hydrogels are prepared with chitosan concentration ranging from 0.1 to 2.0 wt/v %, based on the total composition.

Lower concentrations of chitosan do not allow the formation of a hydrogel and higher concentrations induce the formation of a too firm hydrogel that is not useable.

Preferably, chitosan concentration ranges from 0.5 to 1.0 wt/v %, based on the total composition.

According to step g) of process of the present invention for preparing the composition forming a hydrogel, homogeneously reacetylated chitosan having a molecular weight of not smaller than 200 kDa, preferably not smaller than 600 kDa and a deacetylation degree of 30-60%, preferably 45-55%, is solubilized in an aqueous HCl medium and after complete dissolution of chitosan, the temperature of the chitosan solution is cooled down to a temperature lower than 5° C., for example in an ice-bath.

A higher temperature would induce the precipitation of chitosan during its neutralization.

Then, according to step h) of the process of the present invention for preparing the composition forming a hydrogel, the pH of the chitosan solution is neutralized until pH 6.8-7.2, preferably pH 7 by adding dropwise, under stirring at a temperature lower than 5° C., the required amount of an aqueous solution containing a hydroxylated base previously cooled at a temperature lower than 5° C.

A higher pH would induce the precipitation of chitosan.

A lower pH would not allow a short pseudo-thermogelation time.

According to the present invention, the hydroxylated base used for neutralization is preferably NaOH.

Inadequate stirring or too fast addition of aqueous hydroxylated base induce the precipitation of chitosan.

After complete addition of the hydroxylated base, the pseudo-thermosetting neutralized chitosan composition may be kept under stirring for 10 minutes at temperature lower than 5° C.

The pseudo-thermosetting neutralized chitosan composition of the present invention can be stored at a temperature lower than 5° C. for up to 1 month while gelation may progressively occur during longer storage.

When the temperature of the pseudo-thermosetting neutralized chitosan composition is increased, for example after administration, pseudo-thermogelation occurs leading to the formation of a phosphate-free, transparent firm hydrogel. The higher is the temperature, the shorter is the gelation time.

The process for preparing the pseudo-thermosetting neutralized chitosan composition according to the present invention may further comprise, if required, a step of sterilizing the homogeneously reacetylated chitosan before the step g) of solubilization. To obtain a sterile hydrogel, the preparation is performed under aseptic conditions (e.g. under a laminar flow) and every added solution is previously filtered through a 0.22 μm filter.

For example, sterilization may be performed by radiation or ideally by steam sterilization of homogeneously reacetylated chitosan suspended in water, as described by Yen (Yen S.F. et al., 2001, U.S. Pat. No. 5,773,608).

If desired, the consistency of the phosphate-free, transparent chitosan hydrogel of the present invention may be increased by further adding before, during or after the solubilization, or before, during or after neutralization of the chitosan solution, an appropriate amount of a diol having at least a distance of 4.7 Å between its hydroxyl groups.

Preferably, the diol added is 1,3-propanediol.

The amount of diol added will depend on the required degree of consistency of the hydrogel.

The gelation mechanism of the pseudo-thermosetting neutralized chitosan composition of the present invention is driven by neutralization of chitosan at low temperature. When temperature increases, the global pKa of chitosan decreases, which decreases its global charge density. This allows the formation of direct interactions (e.g. hydrogen bridges or hydrophobic interactions) between polymeric chains.

Therefore, gelation is not induced by a rise of temperature but is favored by a rise of temperature, further decreasing the global charge density through a decrease of the global pKa of chitosan, leading to pseudo-thermogelation.

In the prior art, using β-GP to neutralize chitosan appears only useful to prevent the precipitation of non-reacetylated chitosan during neutralization.

In the present invention, since homogeneously reacetylated chitosan is soluble enough to not precipitate at neutral pH, the addition of β-GP is not required and neutralization may be advantageously performed with any hydroxylated base such as NaOH.

In order to demonstrate the improved elastic properties of the phosphate-free, transparent chitosan hydrogels of the present invention, measurements of viscoelastic properties of two hydrogels according to the invention and of one comparative hydrogel have been performed according to the following method.

Viscoelastic properties of hydrogels were determined immediately after preparation of the hydrogels using a Rheostress 1 (Haake, Karlsruhe, Germany) using a cone/plate device (diameter 60 mm, angle 4°). Temperature was controlled with a thermostatic bath Haake DC 30 and a cooling device Haake K10 (Haake, Karlsruhe, Germany) coupled with the rheometer. Hydrogels were placed between the cone and plate (cooled down at 4° C.) and measured after 10 minutes. All measurements were performed in the linear viscoelastic range and G' and G" were determined under a constant deformation ($\gamma=0.05$) at 1.00 Hz as the temperature was increased from 4 to 37° C. at 1° C./min. over a period of 120 minutes. Temperature of the hydrogel was checked at the beginning and at the end of the measurement with a thermometer probe (RS-232, Extech Instruments, Waltham, USA). Evaporation of water leading to drying of hydrogels was minimized by use of a cover surrounding the cone/plate device.

Hydrogels tested were:
- the phosphate-free, transparent chitosan hydrogel of the present invention obtained in Example 6, containing 0.75% of chitosan (DD=48.6), neutralized at pH 7 by addition of NaOH;
- the phosphate-free, transparent chitosan hydrogel of the present invention obtained in Example 7, containing 0.75% of chitosan (DD=48.6), added with 2.0 ml of 1,3-propanediol and neutralized at pH 7 by addition of NaOH;
- the comparative phosphate-containing, turbid chitosan hydrogel obtained in Example 10 (Comparative), containing 0.75% of chitosan (DD=83.2%) neutralized at pH 7 by addition of β-GP.

The elastic modulus (G') of the tested hydrogels as a function of time when temperature increases from 4 to 37° C. are reported in the Figure. G" is not represented to clarify the presentation of the Figure.

As shown by the Figure, the G' values are much smaller in the comparative chitosan hydrogel neutralized with β-GP than in the chitosan hydrogels neutralized with NaOH according to the present invention.

Further, as shown by the Figure, addition of a diol in the hydrogel according to the present invention further increases the G' values of the hydrogel as compared with the same hydrogel not added with a diol.

These results show clearly that the viscoelastic properties of the phosphate-free, transparent chitosan hydrogels according to the present invention are increased as compared with phosphate-containing chitosan hydrogels known from the prior art.

Further, these results show that viscoelastic properties of phosphate-free, transparent chitosan hydrogels according to the present invention are further increased by adding a diol.

The following examples are intended to illustrate the present invention. However, they cannot be considered in any case as limiting the scope of the present invention.

EXAMPLES

In the following examples, the deacetylation degree of chitosans was determined by the spectrophotometric method described by R. A. Muzarelli and R. Richetti in "Chitin in Nature and Technology", Plenum Press 385-388, 1986 and the molecular weight of chitosans was determined by size exclusion chromatography as reported by O. Felt, P. Furrer, J. M. Mayer, B. Plazonnet, P. Burri and R. Gurny in *Int. J. Pharm.* 180 ,185-193 (1999).

Further, in the following examples, the turbidity of hydrogels was measured at 620 nm with a UV spectrophotometer using formazin suspensions as standards. Briefly, hydrazine sulfate was reacted with hexamethylenetetramine to induce formazin precipitation. Standards of known formazin turbidity units (FTU) were prepared by appropriate dilution.

Example 1

Preparation of a Homogeneously Reacetylated Chitosan Having a DD of 30.4%

The preparation of a homogeneously reacetylated chitosan having a DD of 30.4% started from a chitosan of pharmaceutical grade having a DD of 83.2% and a MW of 1'100 kDa (Aldrich Chemical, Milwaukee, USA).

10.0 g of chitosan were solubilized in 1000 ml of 10% acetic acid/methanol (20/80) mixture and successively filtered through 100 μm and 5 μm filters. Chitosan was precipitated by addition under stirring of 0.2 M NH$_4$OH/methanol (50/50) and washed 4 times with 3000 ml of methanol. Chitosan was dried for 3 days in the presence of Silicagel, under vacuum, at room temperature and protected from light. 1000.0 mg of filtrated chitosan were solubilized in 90.0 ml of 10% acetic acid/methanol (20/80) mixture. After complete dissolution, the solution was cooled down in an ice-bath. Reacetylation was performed in an ice-bath. 360 μl of cold acetic anhydride were mixed in 10.0 ml of cold methanol and this mixture was immediately added drop by drop to the chitosan solution under fast stirring. The solution was kept under stirring for 1 h in the ice-bath and turned into a gel that was left at room temperature for 7 h. This gel was transferred into dialysis bags for dialysis against 2 l deionized water for 1 week. The water was changed twice a day. At the end of the purification step, the gel turned into a viscous solution, which was filtered through a 100 μm filter.

Reacetylated chitosan was precipitated by addition of 0.2 M NH$_4$OH/methanol (50/50) under stirring and washed 4 times with 300 ml of methanol. Reacetylated chitosan was dried for 3 days in the presence of Silicagel, under vacuum, at room temperature and protected from light. At the end of the process, its DD was equal to 30.4%.

Example 2

Preparation of a Hydrogel from a Homogeneously Reacetylated Chitosan Having a DD of 30.4%, Neutralization with NaOH The hydrogel was prepared by the solubilization of 75.0 mg of chitosan obtained in Example 1 in a mixture of 1.0 ml of HCl 0.5N and 4.0 ml of deionized water. The solution was kept under stirring for 48 h at room temperature to allow complete chitosan solubilization. NaOH 0.1N previously cooled down in an ice-bath was added under stirring drop by drop to adjust the pH to 7.0 in an ice-bath. The volume was completed to 10.0 ml with water and the hydrogel was kept under stirring for 10 minutes in an ice-bath. The phosphate-free hydrogel thus obtained was transparent and had a turbidity of 3000 NTU at 37° C.

Example 3 (Comparative)

Preparation of a Homogeneously Reacetylated Chitosan Having a DD of 64.9%

The preparation of a homogeneously reacetylated chitosan having a DD of 64.9% started from a chitosan of pharmaceutical grade having a DD of 83.2% and a MW of 1'100 kDa (Aldrich Chemical, Milwaukee, USA). It was performed as described in Example 1, except that the quantity of acetic anhydride was here equal to 200 µl. At the end of the process, its DD was equal to 64.9%.

Example 4 (Comparative)

Preparation of a Hydrogel from a Homogeneously Reacetylated Chitosan Having a DD of 64.9%, Neutralization with NaOH The hydrogel containing a chitosan with a DD of 64.9% was prepared as described in Example 2, except that the chitosan used was here the chitosan obtained in Example 3. The phosphate-free hydrogel obtained was slightly turbid and had a turbidity of 9700 NTU at 37° C.

Example 5

Preparation of a Homogeneously Reacetylated Chitosan Having a DD of 48.6%

The preparation of a homogeneously reacetylated chitosan having a DD of 48.6% started from a chitosan of pharmaceutical grade having a DD of 83.2% and a MW of 1'100 kDa (Aldrich Chemical, Milwaukee, USA). It was performed as described in Example 1, except that the quantity of acetic anhydride was here equal to 220 µl. At the end of the process, its DD was equal to 48.6%.

Example 6

Preparation of a Hydrogel from a Homogeneously Reacetylated Chitosan Having a DD of 48.6%, Neutralization with NaOH 75.0 mg of chitosan obtained in Example 5 were solubilized in a mixture of 1.0 ml of HCl 0.5N and 4.0 ml of deionized water. The solution was kept under stirring for 48 h at room temperature to allow complete chitosan solubilization. NaOH 0.1N previously cooled down in an ice-bath was added under stirring drop by drop to adjust the pH to 7.0 in an ice-bath. The volume was completed to 10.0 ml with water and the hydrogel was kept under stirring for 10 minutes in an ice-bath. The phosphate-free hydrogel thus obtained was transparent and had a turbidity of 2600 NTU at 37° C. Its viscoelastic behaviour following temperature increase is shown in the Figure.

Example 7

Preparation of a Hydrogel from a Homogeneously Reacetylated Chitosan Having a DD of 48.6%, Neutralization with NaOH, Further Addition of a Diol 75.0 mg of chitosan obtained in Example 5 were solubilized in a mixture of 1.0 ml of HCl 0.5N, 2.0 ml of deionized water and 2.0 ml of 1,3-propanediol. The solution was kept under stirring for 48 h at room temperature to allow complete chitosan solubilization. NaOH previously cooled down in an ice-bath 0.1N was added under stirring drop by drop to adjust the pH to 7.0 in an ice-bath. The volume was completed to 10.0 ml with water and the hydrogel was kept under stirring for 10 minutes in an ice-bath. The phosphate-free hydrogel thus obtained was transparent. Its viscoelastic behaviour following temperature increase is shown in the Figure.

Example 8 (Comparative)

Preparation of a Non-Homogeneously Reacetylated Chitosan Having a DD of 49.0%

The preparation of a non-homogeneously reacetylated chitosan having a DD of 49.0% started from a chitosan of pharmaceutical grade having a DD of 83.2% and a MW of 1'100 kDa (Aldrich Chemical, Milwaukee, USA). It was performed as described in Example 1 for a homogeneously reacetylated chitosan, but there was no previous filtration before reacetylation. Furthermore, reacetylation was performed at room temperature under low stirring and acetic anhydride was not diluted in methanol before addition. The quantity of acetic anhydride was here equal to 300 µl. At the end of the process, its DD was equal to 49.0%.

Example 9 (Comparative)

Preparation of a Hydrogel from a Non-Homogeneously Reacetylated Chitosan Having a DD of 49.0%, Attempt of Neutralization with NaOH, Neutralization with β-GP As the non-homogeneously reacetylated chitosan obtained in Example 8 precipitated at neutral pH after neutralization with NaOH, a hydrogel was prepared following the method described by Biosyntech. Consequently, neutralization was performed by addition of β-GP instead of NaOH.

75.0 mg of chitosan obtained in Example 8 (Comparative) were solubilized in 5.0 ml of 0.1N HCl at room temperature for 48 h. After complete dissolution, this solution was cooled down in an ice-bath. A solution of 1000.0 mg of β-GP in 5.0 ml of deionised water was prepared at room temperature and cooled down in an ice-bath. The β-GP solution was added to the chitosan solution under stirring drop by drop in an ice-bath, which adjusted the pH to 7.0. The hydrogel was kept under stirring for 10 minutes in an ice-bath. The hydrogel thus obtained contained phosphate, was slightly turbid and had a turbidity of 4300 NTU at 37° C.

Example 10 (Comparative)

Preparation of a Hydrogel from a Commercial Chitosan Having a DD of 83.2%. Neutralization with β-GP 75.0 mg of chitosan having a DD of 83.2% and a MW of 1'100 kDa (Aldrich Chemical, Milwaukee, USA) were solubilized in 5.0 ml of 0.1N HCl at room temperature for 48 h. After complete dissolution, this solution was cooled down in an ice-bath. A solution of 1000.0 mg of β-GP in 5.0 ml of deionized water was prepared at room temperature and cooled down in an ice-bath. The β-GP solution was added to the chitosan solution under stirring drop by drop in an ice-bath, which adjusted the pH to 7.0. The hydrogel was kept under stirring for 10 minutes in an ice-bath. The hydrogel thus obtained contained phosphate, was completely turbid and had a turbidity of 15600 NTU at 37° C. Its viscoelastic properties following temperature rise can be seen in the Figure.

Example 11 (Comparative)

Preparation of a Hydrogel from a Commercial Chitosan Having a DD of 83.2% Attempt of Neutralization with NaOH 75.0 mg of chitosan having a DD of 83.2% and a MW of 1'100 kDa (Aldrich Chemical, Milwaukee, USA) were solubilized in 5.0 ml of 0.1N HCl at room temperature for 48 h. After complete dissolution, this solution was cooled down in an ice-bath. NaOH 0.1N was added under stirring drop by drop, but after the addition of a few drops, chitosan started to precipitate. It was therefore impossible to prepare a hydrogel.

The invention claimed is:

1. A homogenously reacetylated chitosan having a molecular weight of not smaller than 200 kDa and a deacetylation degree of 30-60% for use in the preparation of a pseudo-thermosetting neutralized chitosan composition forming a phosphate-free transparent hydrogel at a temperature higher than 5° C., wherein said homogenously reacetylated chitosan is obtained by a homogenous reacetylation process of a chitosan having a molecular weight of not smaller than 200 kDa and a deacetylation degree of 80 to 90%, which process comprises:

filtrating a chitosan having a molecular weight of not smaller than 200 kDa and a deacetylation degree of 80 to 90% dissolved in an acidic medium to eliminate insoluble particles;

precipitating chitosan contained in the filtrated acidic solution to obtain chitosan free of insoluble particles;

preparing a cooled acidic solution of the chitosan free of insoluble particles at a temperature lower than 5° C. to obtain a cooled acidic solution of chitosan free of insoluble particles;

preparing a cooled acetic anhydride solution containing a predetermined amount of acetic anhydride in methanol at a temperature lower than 5° C.;

reacetylating chitosan by adding dropwise, under homogenous conditions, the cooled acetic anhydride solution to the cooled acidic solution of chitosan free of insoluble particles to provide a crude homogenously reacetylated chitosan having a deacetylation degree of 30-60%;

treating said crude chitosan to eliminate salts produced during reacetylation and insoluble particles of chitosan to obtain a homogenously reacetylated chitosan having a deacetylation degree of 30-60%.

2. The homogenously reacetylated chitosan according to claim 1, wherein treating includes:

dialyzing the chitosan obtained to eliminate salts produced during reacetylation in order to obtain a homogenously reacetylated chitosan solution;

filtrating the chitosan solution obtained to eliminate insoluble particles of chitosan;

precipitating the chitosan contained in the filtrated solution obtained and then drying the chitosan to obtain a homogenously reacetylated chitosan having a deacetylation degree of 30-60%.

3. The homogenously reacetylated chitosan according to claim 1, wherein precipitating includes addition of a mixture of $NH_4OH$/methanol.

4. A homogenously reacetylated chitosan having a molecular weight of not smaller than 200 kDa and a deacetylation degree of 30-60% for use in the preparation of a pseudo-thermosetting neutralized chitosan composition forming a phosphate-free transparent hydrogel at a temperature higher than 5° C., wherein the homogenously reacetylated chitosan is derived from a chitosan having a molecular weight of not smaller than 200 kDa and a deacetylation degree of 80 to 90%.

* * * * *